United States Patent [19]

Callingham et al.

[11] 4,066,746

[45] Jan. 3, 1978

[54] REDUCING THE DRYING TIME OF HAIR WITH FLUORINE-CONTAINING VINYL POLYMERS

[75] Inventors: Martin Callingham, Richmond; Kenneth Vasey Curry, Camberley, both of England

[73] Assignee: Lever Brothers Company, New York, N.Y.

[21] Appl. No.: 623,166

[22] Filed: Oct. 16, 1975

Related U.S. Application Data

[63] Continuation of Ser. No. 458,150, April 5, 1974, abandoned, which is a continuation of Ser. No. 265,940, June 20, 1972, abandoned, which is a continuation-in-part of Ser. No. 819,449, April 25, 1969, abandoned.

[30] Foreign Application Priority Data

May 1, 1968 United Kingdom ............... 20651/68
June 13, 1968 United Kingdom ............... 28145/68

[51] Int. Cl.$^2$ ..................... A61K 7/06; A61K 7/135
[52] U.S. Cl. .......................................... 424/62; 8/10; 8/10.1; 8/10.2; 8/11; 132/7; 424/DIG. 2; 424/70; 424/71; 424/72; 424/81

[58] Field of Search ..................... 8/10.1, 10.2, 10, 11; 424/70, 71, 72, DIG. 2, 81, 62; 132/7

[56] References Cited

U.S. PATENT DOCUMENTS

| | | | |
|---|---|---|---|
| 2,803,615 | 8/1957 | Ahlbrecht et al. | 260/29.6 F |
| 3,068,187 | 12/1962 | Bolstad et al. | 260/29.6 F |
| 3,100,180 | 8/1963 | Smith et al. | 424/78 |
| 3,329,661 | 7/1967 | Smith et al. | 260/79.3 M |
| 3,330,812 | 7/1967 | Smith et al. | 260/79.3 M |
| 3,403,122 | 9/1968 | Sherman et al. | 260/29.6 |

FOREIGN PATENT DOCUMENTS

| | | | |
|---|---|---|---|
| 857,689 | 1/1961 | United Kingdom | 260/79.3 M |
| 1,049,003 | 11/1966 | United Kingdom | 424/78 |

*Primary Examiner*—Albert T. Meyers
*Assistant Examiner*—Vera C. Clarke
*Attorney, Agent, or Firm*—Kenneth F. Dusyn; James J. Farrell; Melvin H. Kurtz

[57] ABSTRACT

A method of treating hair on the head to reduce the time required for the drying thereof when wet comprising applying to the hair a polymer derived from an (N-alkyl perfluoroalkanesulphonamido)-ethyl acrylate or methacrylate monomer.

5 Claims, No Drawings

4,066,746

REDUCING THE DRYING TIME OF HAIR WITH FLUORINE-CONTAINING VINYL POLYMERS

BACKGROUND OF INVENTION

Field of the Invention

This application is a continuation of application Ser. No. 458,150, filed Apr. 5, 1974, now abandoned; which is a continuation of application Ser. No. 265,940, filed June 20, 1972, now abandoned; which itself is a continuation-in-part of application Ser. No. 819,449, filed Apr. 25, 1969, now abandoned.

This invention relates to a method for the treatment of hair and more particularly to compositions for the treatment of hair.

Description of the Prior Art

In many treatments applied to hair on the head, especially ladies' hair, the hair is made wet. The drying of the hair following such treatment is a time-consuming operation and may take up a high proportion of the treatment time.

BRIEF SUMMARY OF THE INVENTION

It is an object of this invention to substantially reduce the time required for the drying operation following treatments of the hair involving making the hair wet.

It is also an object of this invention to provide novel hair cosmetic preparations for applying to wet hair on the head to reduce the time required for drying thereof which are acceptable to the consumer.

We have now discovered that these and other objects can be achieved by applying to the hair a known vinyl polymer derived from a fluorine-containing monomer of the general formula

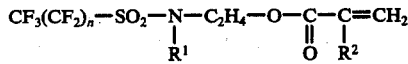

where
R¹ is an alkyl group containing 1 to 6 carbon atoms, e.g. ethyl or propyl,
R² is hydrogen or methyl, and n is an integer from 3 to 11.

Accordingly, in its broadest aspect, the invention provides a method of treating hair on the head to reduce the time required for the drying thereof when wet, which comprises applying thereto in a cosmetically acceptable carrier suitable for application to the human hair an effective amount of a vinyl polymer derived from a fluorine-containing monomer of the general formula

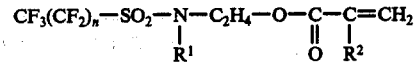

where
R¹ is an alkyl group containing 1 to G carbon atoms, e.g. ethyl or propyl,
R² is hydrogen or methyl, and n is an integer from 3 to 11.

In a second aspect the invention provides a hair cosmetic preparation containing from about 0.0001% to about 5% by weight of the vinyl polymer described above in a cosmetically acceptable carrier suitable for application to human hair.

By the term "a cosmetically acceptable carrir suitable for application to human hair" is meant a composition intended to be applied to the hair for cleansing, beautifying, promoting attractiveness or for altering the appearance of the hair. Examples of such compositions are hair shampoos, waving, setting, bleaching, coloring, conditioning and hairdressing products.

As stated above, the vinyl polymers employed in this invention are known polymers. They are formed by vinyl polymerization, that is by free radical catalyzed polymerization of terminally unsaturated monomers. Their preparation and properties are described in U.S. Pat. Nos. 2,803,615, 3,068,187, and 3,100,180.

The monomer compounds of the general formula given above are the acrylate esters and methacrylate esters of perfluoroalkanesulphonamido alkanols that have in the molecule a perfluorocarbon "tail" containing 4 to 12 fully fluorinated carbon atoms. The parent alcohols may be referred to as N-alkyl,N-alkanol perfluoroalkanesulphonamides and are represented by the formula

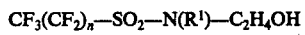

where R¹ and n are as defined above.

The esters readily polymerize inter se to form fluorocarbon polyacrylate and polymethacrylate homopolymers in which the skeletal chain of the polymer molecule is provided with fluorocarbon ester side-chains which have a perfluorocarbon "tail" containing from 4 to 12 fully fluorinated carbon atoms. The structure of the polymer molecule is indicated by the following formula of the recurring ester unit:

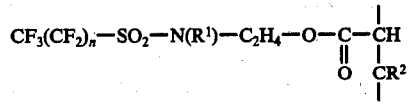

Bulk, solution and emulsion polymerization procedures can be used, employing peroxide and persulphate catalysts.

The fully polymerized homopolymers include clear, colorless, water-repellent and oil-repellent, thermoplastic solids which are flexible and more or less rubbery, which are insoluble in hydrocarbons and other organic solvents and are resistant to swelling therein. They are highly insoluble in water and resistant to swelling therein. They are soluble in fluorinated solvents such as fluorocarbon acids and esters, benzotrifluoride and xylenechexafluoride.

In addition to homopolymers of the aforesaid acrylate and methacrylate esters, copolymers (heteropolymers) can be made by interpolymerizing the ester monomers with polymerizable monomers of kinds which contain an ethylenic linkage. Examples of the latter are maleic anhydride, acrylonitrile, vinyl acetate, vinyl chloride, vinyl silicones, styrene, methyl acrylate, methyl methacrylate, ethylene, isoprene and butadiene; both as to non-halogenated and halogenated varieties. The monomers readily copolymerize with such comonomers, the presence of the fluorocarbon "tail" in the molecular structure of the monomers having been found not to interfere. This makes possible the production of many types of polymers having different physical properties wherein the polymer molecules include fluorocarbon ester units providing perfluorocarbon side-chain "tails" of the type mentioned above.

In addition to the above described substantially homogeneous homopolymers and copolymers, the vinyl polymers of this invention may include block or graft copolymers.

The choice of the method by which the polymers of this invention are manufactured will largely determine the molecular weight range produced. The most generally convenient method of manufacture of the vinyl polymers concerned here is emulsion polymerization. This generally results in a polymer having an average molecular weight range of from 20,000 to 1,000,000. We prefer that the polymer should have an average molecular weight range of from 100,000 to 500,000.

The monomer ratios in the case of a polymer containing the above described fluoromonomer and a single comonomer are generally preferred to be in the range 10:1 to 1:1 with 3:1 being most preferred. In the case of polymers containing two comonomers the proportion of the two comonomers is preferred to be in the range 10:1 to 1:1 and the ratio of total comonomer to fluoromonomer in the range 1:10 to 1:1.

Examples of fluorine-containing monomers from which the polymers employed in this invention are produced are (N-propyl perfluorooctanesulphonamido)-ethyl acrylate and (N-ethyl perfluorooctanesulphonamido)-ethyl methacrylate.

The monomers and their polymers are available from the Minnesota Mining and Manufacturing Company of St. Paul, Minn., USA.

One particular form of the cosmetically acceptable carrier suitable for application to the human hair is that of a shampoo. A shampoo, which may be in liquid, paste or gel form, can contain the usual soaps and detergents in conventional amounts. These should be selected from the group consisting of water-solvent soluble or dispersible anionic detergents, nonionic detergents cationic detergents, ampholytic detergents, sodium, potassium, ammonium or alkylamine soaps of $C_{12}C_{21}$ fatty acids, the soaps of shelloic or abietic acids, and mixtures thereof.

Examples of suitable anionic detergents would include alcohol sulphates, ethoxylated alcohol sulphates, sulphates and sulphonates of ethoxylated phenols, sulphates of fatty esters, sulphates and sulphonates of oils and fatty acids, alkylaryl sulphonates, sulphonates of benzene, toluene and xylene, sulphonates of condensed naphthalenes, sulphonates of dodecyl and tridecyl benzenes, sulphonates of naphthalene and alkyl naphthalene, sulphonates of petroleum, tridecyl and benzene sulphonic acids, taurates (amide sulphates), alkyl sulphonates, and isethionates. Preferred anionic detergents are the sodium, magnesium, ammonium, mono- di- and tri-ethanolamine salts of sulphated fatty alcohols as well as these salts of a sulphonated alkylaryl compounds, all of which have a total of from 12 to 21 carbon atoms. Included herein would be sodium lauryl sulphate, sodium oleyl succinate, ammonium lauryl sulphosuccinate, sodium lauryl ether sulphate, ammonium lauryl sulphate, monoethanolamine lauryl sulphate, triethanolamine lauryl sulphate, sodium dodecyl benzene sulphonate, triethanolamine dodecyl benzene sulphonate, sodium N-lauryl sarcosinate, triethanolamine lauratemyristate and triethanolamine oleate. Suitable nonionic detergents would include tertiary amine oxides, alkylolamides, ethoxylated alcohols, ethoxylated phenols, ethoxylated fatty acids, ethoxylated fatty esters and oils, fatty esters (other than glycerol, glycol, etc.) glycerol esters, and dialkyl sulphoxides. Typical of these compounds are those having 10 to 21 carbon atoms, such as lauric diethanolamide, coconut oil monoethanolamide and lauric isopropanolamide; $C_{10}$–$C_{21}$ fatty alcohols condensed with 3 to 20 moles of ethylene oxide such as the ethylene oxide condensates of lauryl alcohol, myristyl alcohol and palmityl alcohol; and the alkylene oxide condensates of alkyl phenols having a $C_8$–$C_{15}$ alkyl group condensed with 3 to 20 moles of ethylene oxide, such as octylphenol-8 mole ethylene oxide condensate, the nonyl phenol-10 mole ethylene oxide condensate, and the dodecyl phenol-10 mole ethylene oxide condensate.

Cationic compounds suitable for use in a surfactant system according to the present invention would include quaternary ammonium compounds of as well as non-quaternary cationic compounds. Suitable ampholytic detergents would include amino and carboxy (non-quaternary) compounds and betaines such as N-lauryl-N'-carboxymethyl-N'-(2-hydroxyethyl) ethylenediamine, coco-beta-alanine and the Miranol compounds described in U.S. Pat. Nos. 2,528,378 and 2,781,354. The above compounds are exemplary of those found useful for the shampoos of the present invention. Other examples, well known to the art, may be found in the literature such as "Surface Active Agents" by Schwartz and Perry and "Surface Active Agents and Detergents" by Schwartz, Perry and Berch, both Interscience Publishers, New York, the disclosures of which are incorporated herein by reference.

The most preferred detergents are the anionic detergents such as triethanolamine lauryl sulphate, sodium lauryl sulphate, sodium lauryl ether sulphate, etc.

The detergent is preferably present in the shampoos in accordance with this invention in amounts of from about 5 to about 30% by weight, based on the total composition, lesser amounts not cleaning well and greater amounts being potentially eye-irritant. More preferably, the shampoos will contain at least 6%, for example from 8 to 30% by weight of the shampoo.

Optionally, the shampoo in accordance with the invention may also contain one or more lather boosters and/or stabilizers in conventional amounts, to increase sudsing power and foam stability. Examples of these would include cocoamide, lauric diethanolamide, lauric isopropanolamide, betaines, sulphobetaines, cocodimethylamineoxide, bis 2-hydroxyethyl cocoamine oxide, methyl cellulose and hydroxypropyl cellulose; the most preferred of these lather additives are cocoamide and bis 2-hydroxyethyl amine oxide. These materials are generally present in the shampoo in amounts of from about 2 to about 15% by weight.

The amount of the vinyl polymer included in the shampoo compositions of this invention may vary from 0.0001 to 5% by weight of the composition. Preferably, the amount of the polymer is from 0.0015 to 1% and a particularly preferred range is from 0.0015 to 0.02% by weight.

Instead of being applied from a shampoo or other cosmetically acceptable carrier suitable for application to human hair, the vinyl polymer may be applied to the hair, for instance after shampooing. In this case the vinyl polymer can be applied (for example in the form of an aerosol spray) as a solution in a suitable innocuous organic solvent or as an aqueous latex emulsion. The vinyl polymer is suitably applied in this manner in the same concentrations as stated above in respect of shampoo compositions.

Examples of suitable innocuous organic solvents are $C_1$-$C_4$ alcohols, for instance ethanol or isopropanol, glycols, for instance propylene glycol and halogenated hydrocarbon solvents such as methylene chloride.

If it is desired to apply the vinyl polymer in the form of an aerosol spray, the usual aerosol propellants may be used. Examples of these are trichlorofluoromethane (Propellant 11), dichlorodifluoromethane (Propellant 12), and symmetrical dichlorotetrafluoroethane (Propellant 114).

A typical sequence of steps in the performance of the invention when the vinyl polymer is applied during a shampooing treatment but not directly from the shampoo itself is: shampoo the hair, towel dry, apply vinyl polymer, allow vinyl polymer to remain in contact with the hair for up to 10 minutes, rinse, and dry.

It has been found that the vinyl polymer is substantive to hair and reductions in drying time have been obtained after four shampooings with a conventional shampoo following the application of the vinyl polymer.

As stated above, in addition to shampoos, the cosmetically acceptable carrier suitable for application to human hair may be a waving, setting, bleaching, coloring, conditioning, or dressing composition.

Waving compositions in accordance with the invention can contain the usual active ingredients in the conventional amounts. Examples of suitable reducing agents for use in these compositions are thioglycollic acid and its derivatives for instance its ammonium salt, beta-mercapto-propionic acid and its salts, thiourea, and N-acyl homocysteine thiolactones (see U.S. Pat. No. 3,533,417 which is incorporated herein by reference). These sulphydryl-containing reducing agents are conventionally formulated into compositions having an alkaline pH, that is a pH of above 7 and desirably from 9 to 11. Conventional neutralisers such as dilute hydrogen peroxide solutions, sodium perborate and perbromate may be used with the waving compositions of this invention.

Setting, dressing and conditioning compositions in accordance with this invention may contain the usual ingredients in conventional amounts. Most setting lotions contain a high proportion of water and are applied to the hair as a wet spray. The hair is subsequently combed and the water distilled off. The result is a so-called water wave. In addition to water the lotions can usually contain a glossing agent such as a Ucon oil and optionally a substance intended to produce a limited hold on the hair. Dressing compositions are usually alcoholic solutions of vegetable oils, for example castor oil, or of fatty substances such as oleyl alcohol and isopropyl myristate. These are applied to the hair and the hair is then combed with a wet comb to precipitate a fine dispersion of the oil on the hair. Conditioning agent compositions generally contain cationic substances such as quaternary ammonium salts. These are substantive to the hair and produce a conditioning effect.

The bleaching agent which is almost univerally used in bleaching compositions and which is also useful in the bleaching compositions of this invention is hydrogen peroxide. For home use bleaching compositions comprise a 3–4 per cent solution of hydrogen peroxide. For professional use the solution is more concentrated, that is 5–6 per cent. Hydrogen peroxide is unstable and so in order to impart a satisfactory shelf life to the compositions they are stabilized by for example dilute acids, acetanilide, and sequestering agents. Conditioning agents such as quaternary ammonium salts and lanolin derivatives are also frequently added to bleaching compositions. Immediately before use bleaching compositions are mixed with ammonia solution. This swells the hair and neutralizes the hydrogen peroxide which begins to liberate oxygen very rapidly.

The coloring compositions of this invention may be permanent or semi-permanent. Permanent hair colorants are typically formulated on oxidation dyes. The compositions generally contain (1)dye-intermediates, for example ortho- or para-diamines and ortho- or para-aminophenols. These form a strong coloration on oxidation. (2) Color modifiers for example meta-diamines, meta-aminophenols, phenols and pyrazolones. These do not form a color on their own but when oxidised in the presence of the above dye-intermediates do so. (3) An oxidiser. This is, of course, packaged separately. Examples of the commonly used oxidising agents are hydrogen peroxide solution, sodium perborate and sodium persulphate. The colorant compositions also contain stabilisers and detergents.

Semi-permanent colorant are generally formulated on direct dyestuffs although other types, for example basic dyestuffs and reactive dyestuffs have been proposed. Typical direct dyestuffs for use in semi-permanent colorant compositions are nitro dyes, anthraquinone dyes, napthoquinone dyes and azo dyes. The most commonly used nitro dyes are the 1,2,4,-trisubstituted benzenes having one nitro group and two electron-donor substituents such as hydroxy, methoxy, amino, or substituted amino. Hydroxy alkylated amino derivatives have been particularly popular. Anthraquinone dyes generally include quaternary ammonium groups. Amongst these the dialkylaminoalkylamino(DAAA) group and its quaternized variants have been included in a variety of anthraquinone dyestuffs. The anthraquinones can be solubilised by the incorporation of polyoxyethylene side chains or by the incorporation of acidic groups. Amongst the napthoquinone dyes those most frequently proposed for use in dyeing hair contain hydroxy groups. Examples of these are 5-hydroxy-1,4-napthoquinone and 5,6,8-trihydroxynapthoquinone. Of the azo dyes, yellow to red-violet and black dyes are obtained by coupling dimethylamino anilines with N,N-dimethyl aniline or with napth lamine and quaternizing the dye, while brown-brown/black dis-azo dyes are similarly obtained using polyaminonapthalines as couplers. Semi-permanent colorant are usually formulated as a so-called "single cavity" product, that is one which is contained in a single vessel such as in a jar or bottle or in a tube. This is in contrast to permanent colorant based on oxidation dyes which are two-pack products. Semi-permanent colorant compositions contain a detergent system. This is generally based on nonionic or amphoteric detergents.

DESCRIPTION OF SPECIFIC EMBODIMENTS

The following is a description of experiments that have been performed demonstrating the advantageous effect of treating hair with the above vinyl polymer. Percentages are by weight.

Experiment I

A 6 g. switch of ether-extracted hair was left for 10 minutes in contact with a treatment liquid containing a vinyl polymer. The switch as dried using a hair drier and then soaked for 15 minutes in water. The wet switch was then shaken to remove surface water and suspended in an enclosure heated to 45° C. The switch was weighed at various intervals and the time taken for the switch to dry to a constant weight was noted. Similar data were obtained for a control switch: this was treated with water instead of the vinyl polymer. The drying time of the treated switch was expressed as a fraction (hereafter called the drying time value) of the drying time for the control switch.

The vinyl polymers used in this experiment were a copolymer of (N-ethyl perfluorooctanesulphonamido)-ethyl methacrylate (3 parts) and chloroprene (1 part) (polymer I) and a copolymer of (N-ethyl perfluorooctanesulphonamido)-ethyl methacrylate (3 parts) and a mixture of methyl methacrylate and higher alkyl esters of acrylic acid (1part) (polymer II). The results obtained with polymers I and II are indicated in Table I below. The treatment liquid was in each case an aqueous latex containing 3% polymer solids.

Table I

| Polymer | Drying Time Value |
|---|---|
| I | 0.50 |
| II | 0.80 |

Experiment II

A switch was treated as in Experiment I with an aqueous emulsion of Polymer I containing 3% polymer solids and then shampooed a number of times with a conventional shampoo. After each shampooing the drying time value was determined. The results are given in Table II.

Table II

| | Drying Time Value |
|---|---|
| After vinyl polymer treatment | 0.58 |
| After 1st shampooing | 0.58 |
| After 2nd shampooing | 0.50 |
| After 3rd shampooing | 0.58 |
| After 4th shampooing | 0.75 |

Experiment III

In this experiment the effect of concentration of the vinyl polymer in the treatment liquid was investigated. 6 g. switches of hair were washed with a shampoo containing monoethanolamine lauryl sulphate (12%) and lauric isopropanolamide, and then treated for 10 minutes with 15 mls. of an aqueous emulsion of fluoropolymer. The switches were then thoroughly washed with water, towel dried, and the drying time value determined. The results are given in Table III.

Table III

| % solids in polymer emulsion | Drying Time Value Polymer I | Drying Time Value Polymer II |
|---|---|---|
| 0.0003 | 0.80 | 0.80 |
| 0.003 | 0.33 | 0.80 |
| 0.030 | 0.50 | 0.66 |
| 0.300 | 0.50 | 0.66 |

Experiment IV 6 g. switches of hair were shampooed and rinsed in water. Into the hair was then rubbed the vinyl polymer emulsion employed in Experiment II and this was left on the hair for 10 minutes. The hair was then rinsed in water, towel dried and wound onto rollers. One roller was left to dry in ambient conditions and the other in a heated forced draught. The drying time values were obtained and these are given below in Table IV.

Table IV

| Drying Method | Drying Time Value |
|---|---|
| Heated forced draught | 0.50 |
| Ambient conditions | 0.43 |

Experiment V

Varying amounts of an emulsion of polymer I were stirred into a shampoo base (containing monoethanolamine lauryl sulphate (12%) and lauric isopropanolamide (1.5%), and having pH 7) to give three treatment shampoos containing 0.09%, 0.015%, and 0.006% polymer solids. These were used to wash hair switches, the time of contact between the hair switch and the treatment shampoo being varied. After shampooing, the hair switch was rinsed, towel-dried, weighed at various intervals and the drying time determined as in Experiment I. The results are indicated in Table V below.

Table V

| Concentration | Treatment Time | Drying Time Value |
|---|---|---|
| 0.03% | 10 minutes | 0.33 |
| | 5 minutes | 0.33 |
| | 2 minutes | 0.33 |
| | 1 minute | 0.50 |
| 0.015% | 10 minutes | 0.33 |
| | 5 minutes | 0.50 |
| | 2 minutes | 0.50 |
| | 1 minute | 0.33 |
| 0.006% | 10 minutes | 0.40 |
| | 5 minutes | 0.40 |
| | 2 minutes | 0.60 |
| | 1 minute | 0.40 |

Experiment VI

The pH's of shampoos containing polymer I in an amount of 0.003% polymer solids, and 12% monoethanolamine lauryl sulphate, were adjusted to various levels by the addition of appropriate amounts of sodium hydroxide or hydrochloric acid. Each shampoo (¼ g.) was then used to wash a 6 g. switch of natural untreated hair. The hair was then rinsed, towel-dried, and the drying time value determined as in Experiment I. The results are given below in Table VI.

Table VI

| pH of shampoo | Drying Time Value |
|---|---|
| 2 | 0.50 |
| 3 | 0.33 |
| 4 | 0.33 |
| 5 | 0.50 |
| 6 | 0.50 |
| 7 | 0.50 |
| 8 | 0.66 |
| 9 | 0.66 |
| 10 | 0.66 |

Accelerated drying effects were observed over a wide range of pH values, but for this polymer concentration the most rapid drying of the hair followed treatment at pH 3–4.

Experiment VII

This experiment was carried out in the salon where a model's hair was shampooed, towel-dried and set in rollers, the rollers being put consecutively in alternate sides of the head. The head was then put under an already warmed-up hair drier and the hair was inspected at intervals of 5 minutes for dryness.

When the hair was dry it was immediately shampooed again, towel dried and then treated with 25 ml. of an aqueous emulsion of polymer I, containing about 1.5% polymer solids, which was left on the hair for ten minutes. The hair was then thoroughly rinsed through, towel-dried and set in rollers as before and the time required for the hair to dry again determined as previously. The results are given in Table VII.

Table VII

|  | Before Treatment | After Treatment |
|---|---|---|
| Total drying and inspection time | 52 minutes | 31 minutes |
| Total time under the drier | 40 minutes | 25 minutes |

Thus treatment with the vinyl polymer reduced the drying time of the hair by about 40%.

Experiment VIII

The following is a description of a test carried out on a panel of women. The heads were washed once a week for 8 weeks. For the first 4 washings a base shampoo containing 16% monoethanolamine lauryl sulphate was applied, and for the last 4 washings there was applied the test shampoo consisting of the base shampoo in which 0.003% polymer I solids has been included.

The drying time of the hair was assessed after each washing by feel and appearance.

The procedure for washing and drying the hair was as follows.

2 × 10 ml applications of shampoo were given in each washing. Each application was lathered for 30 seconds, and the hair was then rinsed with water approximately 38° C until all the lather had just gone. The hair was towel dried to the extent that all surplus water was removed. For each panelist, the period from the removal of the towel, until the head was put under the drier was timed for the first shampooing treatment and then adhered to in the following 7 washes.

Photographs were taken after roller insertion during the first treatment as a record of roller pattern, size and number, and this was followed in the following 7 washes.

Each panellist was dried under the same drier (preheated for 30 minutes) at the same setting each week. The hair was assessed for dryness after the first 10 minutes, than after every 5 minutes until the hair was dry. A 2-minute period was allowed each time for this assessment timed from the removal of the drier to its replacement. The assessment was carried out by three observers each time.

Results on 10 of the panelist are given below to Table VIII.

Table VIII

| Base shampoo | Test shampoo | Drying time value | Significance |
|---|---|---|---|
| 24.2 | 17.0 | 0.70 | 1:1000 |
| 18.7 | 10.0 | 0.53 | 1:1000 |
| 61.2 | 27.5 | 0.44 | 1:1000 |
| 52.0 | 45.0 | 0.86 | 1:1000 |
| 48.3 | 29.2 | 0.60 | 1:1000 |
| 36.2 | 20.5 | 0.56 | 1:1000 |
| 34.7 | 18.5 | 0.53 | 1:100 |
| 44.5 | 24.0 | 0.53 | 1:100 |
| 33.3 | 20.5 | 0.61 | 1:100 |
| 49.0 | 38.7 | 0.79 | 1:50 |

Each of the figures in the first two columns is an average of four drying times, and the significance gives the chance of the difference in drying time and being true. This latter figure takes into account the scatter of drying times about the mean.

Experiment IX

A 6 g. switch of untreated natural hair was washed in base shampoo comprising 12% monoethanolamine lauryl sulphate, rinsed and the surplus water removed. The switch was then saturated with 6 g. of a dyeing solution and left for 20 minutes. The switch was then rinsed under running water for 20 seconds and towel dried for 20 seconds. It was then placed under a hair drier and the drying time determined.

The dye solution had the following composition:

|  | % |
|---|---|
| Oxidation dyestuff | 2 |
| Monoethanolamine lauryl sulphate | 20 |
| Polymer I solids | 0 or 0.03 or 0.3 |
| Water | to 100 |
| pH 6 | |

The results are given in Table IX.

Table IX

| % Polymer I solids | Drying Time Value |
|---|---|
| 0.03 | 0.62 |
| 0.3 | 0.75 |

Experiment X

The preceding dyeing and drying procedure was employed using a colourant based on a basic dye of the following composition:

|  | % |
|---|---|
| Methylene Blue (C.I. 52015)* | 2 |
| Dimethyl coco amine oxide | 8 |
| Polymer I solids | 0 or 0.03 or 0.3 |
| Water | to 100 |

*Colour Index Number (Society of Dyers and Colourists, Bradford, Yorks, England)

The results are given in Table X.

Table X

| % Polymer I solids | Drying Time Value |
|---|---|
| 0.03 | 0.62 |
| 0.3 | 0.62 |

Experiment XI

A 6 g. switch of untreated natural hair was washed with a 12% monoethanolamine lauryl sulphate solution. The towel-dried switch was then wound onto a roller and a permanent waving solution applied and left on for 10 minutes. The hair was then rinsed whilst still on the rollers and neutraliser applied for 10 minutes. The hair was then thoroughly rinsed, blotted with a towel and its drying time determined.

The compositions of the permanent waving solution and neutraliser were as indicated below.

| Permanent waving solution | % |
|---|---|
| Thioglycollic acid | 6 |
| Concentrated ammonia solution | 20 |
| Sodium lauryl sulphate | 1 |
| Water | 73 |
| Neutraliser | % |
| Hydrogen peroxide (20 vol) | 20 |

| | |
|---|---|
| Polymer I solids | 0 or 0.003 or 0.3 |
| Water | to 100 |

The results are given in Table XI.

Table XI

| % Polymer I solids | Drying Time Value |
|---|---|
| 0.03 | 0.62 |
| 0.3 | 0.70 |

Experiment XII

A 6 g. switch of untreated natural hair was washed with a 12% monoethanolamine lauryl sulphate solution, rinsed in running water and towel dried for 20 seconds. The switch was then sprayed with an aqueous emulsion of Polymer I from a pump-type spray, and its drying time determined.

The results obtained are given in Table XII.

Table XII

| % Polymer I solids | Drying Time Value |
|---|---|
| 0.03 | 0.47 |
| 0.3 | 0.41 |

Experiment XIII

To a 6 g. switch of untreated natural hair was applied 1 g. of a hair dressing lotion. The time required for the drying of the switch to a constant weight was determined. The compositions of the hair dressing preparations employed in this experiment are indicated below.

| | % |
|---|---|
| Ethyl alcohol | 20 |
| Polyethylene glycol (M.Wt.400) | 10 |
| Polymer I solids | 0 or 0.003 or 0.03 |
| Water | to 100 |

The results obtained are given in Table XIII.

Table XIII

| % Polymer I solids | Drying Time Value |
|---|---|
| 0.003 | 0.75 |
| 0.03 | 0.50 |

The following are further examples of compositions in accordance with the invention comprising a vinyl polymer in a cosmetically acceptable carrier suitable for application to the hair.

EXAMPLE 1

Clear Liquid Shampoo

| | % by weight |
|---|---|
| Monoethanolamine lauryl sulphate | 12.0 |
| Lauric isopropanolamide | 1.5 |
| Polymer I | 0.03 |
| Water | to 100 |

EXAMPLE 2

Pearlescent Cream Lotion Shampoo

| | % by weight |
|---|---|
| Monoethanolamine lauryl sulphonate | 30 |
| Lauric isopropanolamide | 2 |
| Magnesium stearate | 2 |
| Octadecyl alcohol | 1 |
| Polymer II | 0.03 |
| Perfume | 0.4 |
| Distilled alcohol | balance to 100 |

EXAMPLE 3

Cream Paste Shampoo

| | % by weight |
|---|---|
| Sodium lauryl sulphate | 20 |
| Coconut monoethanolamide | 1 |
| Propylene glycol monostearate | 2 |
| Stearic acid | 5 |
| Sodium hydroxide | 0.75 |
| Polymer II | 0.015 |
| Water | to 100 |

EXAMPLE 4

Medium Brown Oxidation Colourant

| | % by weight |
|---|---|
| p-Phenylenediamine | 2.00 |
| o-Aminophenol | 0.20 |
| 4-Nitro-1,2-diaminobenzene | 0.15 |
| p-Aminodiphenylamine | 0.20 |
| Resorcinol | 1.00 |
| $NH_3$ (26° Be=29.4 wt%. $NH_3$) | 10.0 |
| Isopropanol | 2.5 |
| Perfume | 0.5 |
| Oleic acid | 35.0 |
| Polyoxyethylene sorbitan mono-oleate | 10 |
| Nonionic | 3.5 |
| Lanolin | 1.75 |
| Lecithin | 1.25 |
| Chelating agent | 0.25 |
| Polymer II | 0.006 |
| Water | to 100 |

EXAMPLE 5

Bleaching Solution

| | % by weight |
|---|---|
| Hydrogen peroxide | 6 |
| Acetanilide | 0.4 |
| Ethylene diamine tetra-acetic acid | 0.4 |
| Cholesterol | 0.5 |
| Polymer I | 0.015 |
| Water | to 100 |

EXAMPLE 6

Brightening Rinse

| | % by weight |
|---|---|
| $H_2O_2$ (3%) | 97.1 |
| Alkylethyl morpholine ethosulfate | 1.5 |
| Adipic acid | 0.8 |
| Sodium stannate | 0.6 |
| Polymer II | 0.015 |
| | adds to 100 |

EXAMPLE 7

Waving Compositon

| | % by weight |
|---|---|
| Thioglycollic acid | 6.62 |
| Total ammonia (as $NH_3$) | 2.11 |

-continued

| Waving Composition | |
|---|---|
| | % by weight |
| Polymer II | 0.03 |
| Water | to 100 |

EXAMPLE 8

| Waving Composition | |
|---|---|
| | % by weight |
| N-acetyl homocysteine thiolactone | 16 |
| Monoethanolamine | 10.4 |
| Lactic acid | 4 |
| Polymer I | 0.006 |
| Water | to 100 |

EXAMPLE 9

| Conditioner | |
|---|---|
| | % by weight |
| Vinyl acetate/crotonic acid copolymer | 1.20 |
| Castor oil | 0.15 |
| Di-isopropylic ester of adipic acid | 0.50 |
| Colour | 0.50 |
| Perfume | 0.30 |
| Isopropyl alcohol | 75.00 |
| Water | to 100 |

EXAMPLE 10

| Setting Lotion | |
|---|---|
| | % by weight |
| Vinyl acetate/crotonic acid polymer | 8.50 |
| Polyethylene glocyol 5100 | 0.40 |
| Polymer I | 0.006 |
| Perfume | 0.05 |
| Ethyl alcohol | 80.00 |
| Distilled water | to 100 |
| Pressurised with 25% of an equal mixture of difluorodichloromethane and 1,2-dichlorotetrafluoroethane. | |

What is claimed is:

1. A method of treating hair on the head to reduce the time required for the drying thereof when wet, which comprises applying thereto in a cosmetically acceptable carrier suitable for application to human hair an effective amount of a vinyl polymer selected from the group consisting of homopolymers, copolymers, block copolymers and graft copolymers of a fluorine-containing monomer of the formula:

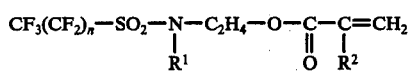

wherein $R^1$ is an alkyl group containing 1 to 6 carbon atoms
$R^2$ is hydrogen or methyl, and $n$ is an integer from 3 to 11, the vinyl polymer having a molecular weight of from 20,000 to 1,000,000, and when the polymer is a copolymer, the ratio of the fluorine-containing monomer to the comonomer or comonomers being from 10:1 to 1:1 and said comonomer being selected from the group consisting of halogenated and non-halogenated maleic anhydride, acrylonitrile, vinyl acetate, vinyl chloride, vinyl silicones, styrene, methyl acrylate, methyl methacrylate, ethylene, isoprene and butadiene.

2. The method defined in claim 1 wherein $R^1$ is selected from the group consisting of ethyl and propyl.

3. The method defined in claim 1 wherein the said fluorine-containing monomer is (N-ethyl perfluorooctanesulphonamido)-ethyl methacrylate.

4. The method defined in claim 1 wherein the vinyl polymer is a copolymer of (N-ethyl perfluorooctanesulphonamido)ethyl methacrylate and chloroprene.

5. The method defined in claim 1 wherein the said carrier is a hair cosmetic preparation selected from the group consisting of hair shampoo, waving, setting, bleaching, coloring, conditioning and hair dressing products.

* * * * *